(12) United States Patent
McConnell-Montalvo et al.

(10) Patent No.: US 6,939,330 B1
(45) Date of Patent: Sep. 6, 2005

(54) SYRINGE INSERTION SYSTEM

(75) Inventors: Susan McConnell-Montalvo, Woodland Hills, CA (US); Jeffrey F. Field, Camarillo, CA (US); April Marano-Ford, Manhattan Beach, CA (US)

(73) Assignee: Medsolve LLC, Manhattan Beach, CA (US)

( * ) Notice: Subject to any disclaimer, the term of this patent is extended or adjusted under 35 U.S.C. 154(b) by 154 days.

(21) Appl. No.: 10/319,419

(22) Filed: Dec. 12, 2002

(51) Int. Cl.[7] ............................................. A61M 5/31
(52) U.S. Cl. ...................... 604/197; 604/198; 128/919
(58) Field of Search .................... 604/40, 117, 130, 604/156, 157, 164.08, 164.12, 187, 192, 604/232, 95.01, 95.02, 134, 136, 181, 218, 604/194–198, 263; 128/919

(56) References Cited

U.S. PATENT DOCUMENTS

| | | | | |
|---|---|---|---|---|
| 3,702,608 | A | * | 11/1972 | Tibbs .......................... 604/136 |
| 4,787,891 | A | * | 11/1988 | Levin et al. ................. 604/136 |
| 5,282,793 | A | * | 2/1994 | Larson ....................... 604/192 |
| 5,389,076 | A | * | 2/1995 | Shaw .......................... 604/110 |
| 5,487,732 | A | * | 1/1996 | Jeffrey ........................ 604/110 |
| 5,658,259 | A | * | 8/1997 | Pearson et al. .............. 604/232 |
| 5,851,197 | A | | 12/1998 | Marano et al. ............. 604/135 |
| 5,938,644 | A | | 8/1999 | Kirk ........................... 604/263 |
| 6,050,977 | A | | 4/2000 | Adams ........................ 604/195 |
| 6,093,172 | A | | 7/2000 | Funderburk et al. ........ 604/135 |
| 6,293,925 | B1 | | 9/2001 | Safabash et al. ............ 604/136 |
| 6,416,497 | B1 | | 7/2002 | Kirk ........................... 604/198 |
| 6,544,234 | B1 | * | 4/2003 | Gabriel ....................... 604/207 |
| 2003/0060781 | A1 | | 3/2003 | Morgensen et al. | |
| 2004/0215151 | A1 | * | 10/2004 | Marshall et al. ............ 604/198 |

OTHER PUBLICATIONS

U.S. Appl. No. 10/330,682, filed Dec. 27, 2002.

* cited by examiner

Primary Examiner—Anhtuan T. Nguyen
Assistant Examiner—Catherine S. Williams
(74) Attorney, Agent, or Firm—Fulbright & Jaworski L.L.P

(57) ABSTRACT

An inserter having a housing, a syringe carriage slidably mounted within the housing and a syringe socket defined within the syringe carriage. The syringe carriage is able to assume a cocked position and an extended position with the latter being the position for injection. A spring biases the syringe carriage to the extended position and a latch selectively retains the syringe carriage in the cocked position.

16 Claims, 5 Drawing Sheets

SYRINGE INSERTION SYSTEM

BACKGROUND OF THE INVENTION

The field of the present invention is systems for automatically placing a syringe needle hypodermically.

Many people find hypodermic injections unpleasant. This is particularly true with self-injections. Systems have been developed for the hypodermic insertion of syringe needles. Such placement is typically accomplished through the release of a spring loaded syringe carriage mounted within a housing. The syringe carriage receives and deploys a standard syringe. The device, frequently referred to as an inserter, is loaded with a syringe, positioned and a trigger mechanism actuated to release the carriage for rapid delivery of the associated syringe needle into the injection position. The injection is then accomplished, either manually by depressing a plunger or automatically through the use of a spring system to depress the plunger. Once the injection is complete, the entire device is simply withdrawn.

Such systems provide for the placement of the needle without the user having to advance the syringe into a hypodermic position. A simple triggering action replaces the act of insertion. Further, the needle is rapidly placed. Rapid placement of a needle hypodermically is perceived to be less painful. Substantial pressure can also be exerted around the injection site by the housing. This can give the perception that there is less pain. Consequently, such systems are a relief to many people receiving injections and particularly where those injections are self-performed.

Looking to the health care provider, the medical industry has contemplated the desirability of protecting personnel from accidental sharps injuries, such as needle sticks. Concerns have been expressed about the possibility of transmitting serious or potentially fatal infections as a result of sharps accidents, even through the manipulation of safety devices into position for protection. Also, concerns have been expressed regarding the vaporizing of body fluids and injection fluids through the rapid acceleration of sharps as they are retracted into safety positions. Legislation requiring the use of safe needle technology is pending in a number of states and before the Occupation Safety and Health Administration. Safe, conveniently used and inexpensive systems are needed which reduce the amount of manual manipulation required to make the needle safe against sharps injuries.

SUMMARY OF THE INVENTION

The present invention is directed to a system for automatically placing needles hypodermically using a housing with a syringe carriage movably mounted therein between a cocked position and an extended position. A syringe socket is provided on the syringe carriage for receipt of available syringes. An insertion spring and a latch cooperate to control and perform the hypodermic placement of the syringe needle.

In a first separate aspect of the present invention, a needle guard may be movably mounted to cover selectively the needle at the needle end of the device. The mounting of the guard may be to the syringe carriage at that needle end. If so mounted, the guard may be biased toward extension from the carriage through the needle access opening and retractable therefrom. This needle guard is intended to abate the risk of a sharps injury following injection. The guard can also be applied to cover a needle as it is removed from the injection site and to cover vaporized fluids created by rapid acceleration of a needle into a safe position.

In a second separate aspect of the present invention, a safety syringe system is contemplated to include a needle release mechanism and needle retraction mechanism associated with a syringe in combination with the inserting system. The injection can be performed, the needle either withdrawn or not at the preference of the user and further force delivered to the plunger for needle retraction.

In a third separate aspect of the present invention, the syringe carriage includes a plunger access opening through which the syringe plunger may extend. This plunger access opening is in the syringe carriage outwardly of the main bore in both the cocked position and the extended position. This provides relief for the plunger access opening for forceful extension of the plunger to the end of the barrel, an action employed for needle retraction on safety syringes.

In a fourth separate aspect of the present invention, a plunger access opening to the syringe socket receives the syringe into the socket and at least one pivotal clip having a flange extendable into the plunger access opening retains the finger grip flange and a lever actuates the flange. This system facilitates rear placement and removal of the syringe.

In other aspects of the present invention, the separate aspects may additionally contemplate novel features admitting of greater inserter utility. The syringe socket may include a side opening to laterally receive an available syringe for an injection. Such a lateral opening can facilitate placement, provide for a clear view of the graduations on the syringe barrel and facilitate the loading operation of the insertion system. The insertion spring may be located in a spring bore adjacent to the main bore to facilitate side loading. Shoulders in the socket may also be arranged to closely capture the finger grip flange of the syringe. A port proximal to the needle access opening in the housing may be sized to receive the end of a standard syringe vial in a location to receive the needle of a syringe with the syringe socket in the cocked position. Stabilization of a syringe and vial during charging of the syringe is contemplated by this arrangement. The latch to release the cocked syringe may extend from the housing proximal the needle access opening in the syringe. A latch position extending from the housing and an unlatched position retracted toward the housing can provide for automatic triggering of the insertion device upon placement and the application of pressure about the injection site.

Finally, any of the foregoing aspects are contemplated to be employed in combination to further advantage.

DETAILED DESCRIPTION OF THE PREFERRED EMBODIMENTS

Figures 1, 2:
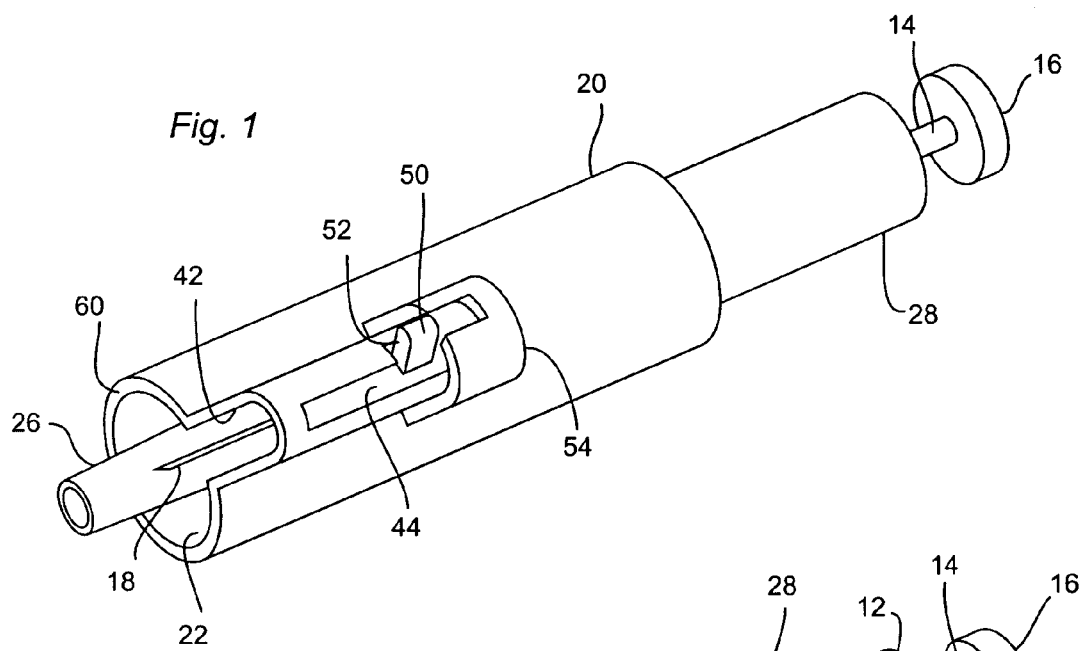
FIG. 1 is a perspective view of a syringe insertion system.
FIG. 2 is a perspective view of the other side of the syringe insertion system of FIG. 1.

Turning in detail to the drawings, a syringe insertion system is illustrated. The system is contemplated to employ conventional syringe structures which may or may not have a needle retraction mechanism offering a safety feature against sharps injuries. A common syringe typically employs a barrel 10 having a finger grip flange 12. A plunger 14 is slidable in the barrel 10 and conventionally extends from one end of the barrel to a thumb button 16. A needle 18 is affixed to the barrel 10 at one end. The syringe may be configured as a safety syringe and thereby include a needle release mechanism and a needle retraction mechanism. Such mechanisms contemplated for employment with the present invention are illustrated in U.S. Pat. No. 5,389,076 and U.S. Pat. No. 6,050,977, the disclosure of which is incorporated herein by reference. The needle release mechanism typically operates through the forced extension of the plunger to the needle end of the barrel. The needle retraction mechanism is operatively engageable with the needle such that when the needle is released, it is drawn back into the barrel of the syringe.

A first insertion system is illustrated in FIGS. 1 through 4. The insertion system, or inserter, includes a housing 20 which is generally cylindrical in form. The housing 20 includes a main bore 22 open at both terminal ends. A longitudinal housing slot 24 extends fully to one end as can be seen in FIG. 2. The slot 24 is wide enough to accommodate a contemplated standard syringe barrel 10 and needle cover 26. The housing 20 is formed in two halves split longitudinally and sonically welded or bonded together to accommodate component assembly within the housing 20.

Figure 3:
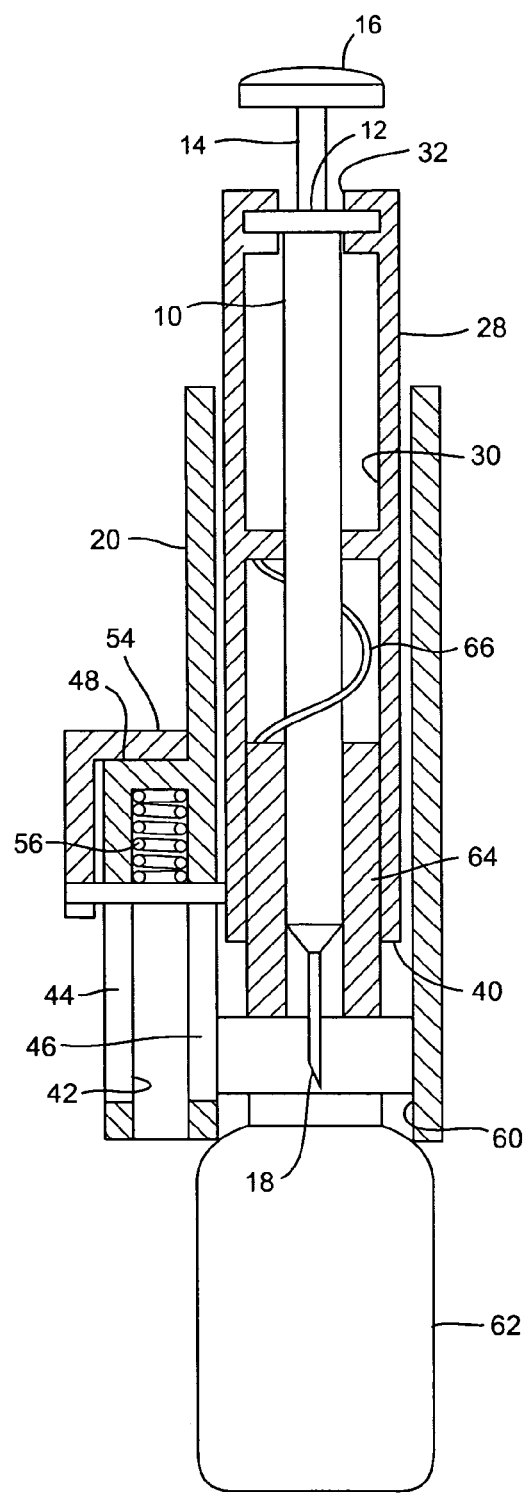
FIG. 3 is a cross-sectional side view of the syringe insertion system of FIG. 1 with the carriage in the cocked position.
Figure 4:
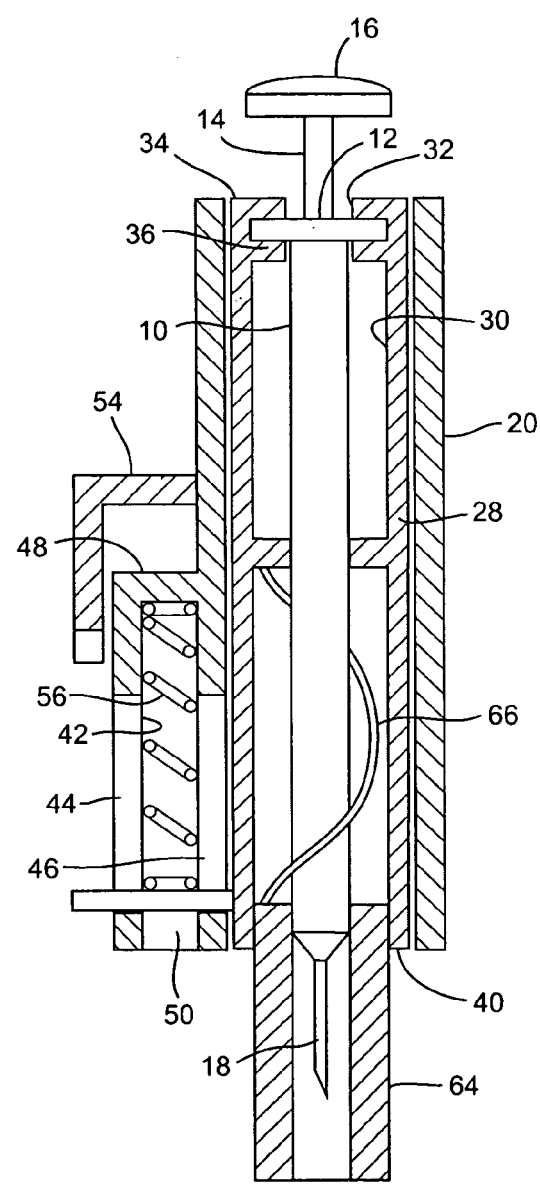
FIG. 4 is a cross-sectional side view as taken in FIG. 3 with the syringe carriage in the extended position.
Figure 5:
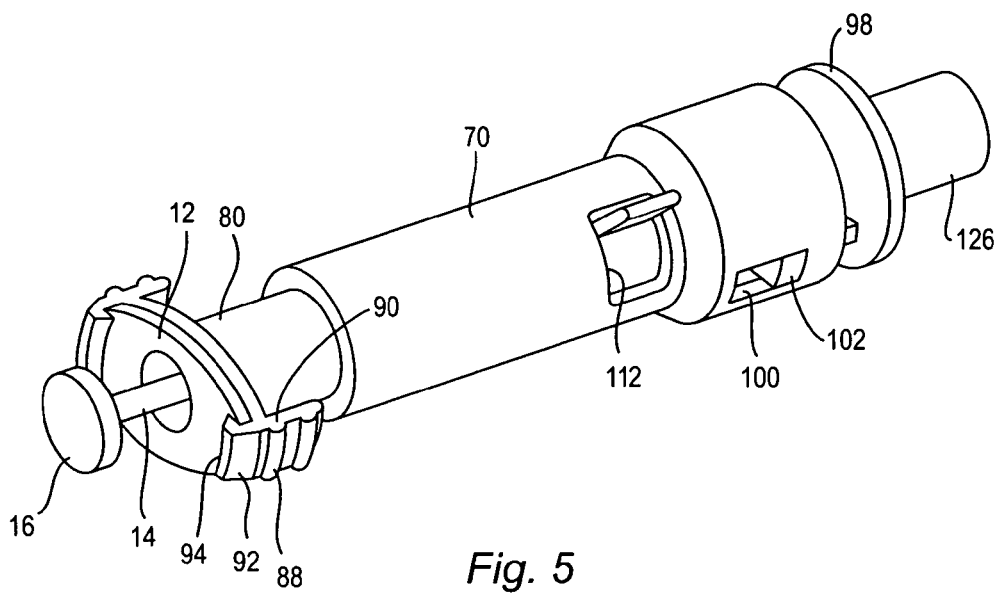
FIG. 5 is a perspective view of a second syringe insertion system.

A syringe carriage 28 is also shown to be generally cylindrical in construction to fit within the main bore 22. The syringe carriage 28 is movably mounted within the main bore 22 and is slidable between a cocked position as seen in FIG. 3 and an extended position as seen in FIG. 4. In the cocked position, the syringe carriage 28 extends outwardly from the main bore proximal the syringe plunger 14. In the extended position, the syringe carriage 28 has moved in the direction of the needle end such that the needle 18 of a syringe carried within the carriage 28 extends beyond the end of the housing 20 to the depth of insertion.

The carriage 28 defines a syringe socket 30 within the interior thereof. A plunger access opening 32 is located in the syringe carriage 28 at the plunger end of the syringe socket 30. Two opposed shoulders are defined between two inwardly extending flanges 34 and 36. These flanges 34 and 36 receive the finger grip flange 12 of a syringe barrel 10. The outermost flange 34 is shown to be flush with the plunger end of the syringe carriage 28. By closely capturing the finger grip flange 12, the syringe barrel 10 is retained longitudinally within the syringe socket 30. A longitudinal carriage slot 38 defines a side opening to laterally receive the syringe barrel 10. The carriage slot 38 is aligned with the housing slot 24 as best seen in FIG. 2 to facilitate receipt of a syringe. The longitudinal carriage slot 38 intersects the plunger access opening 32 and the inwardly extending flanges 34 and 36 to provide access for the finger grip flange 12 to the slot between the shoulders of the flanges 34 and 36.

A needle access opening 40 is located in syringe carriage 28 at the needle end of the syringe socket 30 and is broadly open to the syringe socket 30. The needle access opening 40 need not be tightly constricted around any inserted syringe barrel 10 to facilitate loading the syringe. Some degree of relative lateral motion between the syringe and the inserter may be tolerated without detriment.

Because of the side opening to laterally receive a syringe, the housing 20 conveniently provides a spring bore 42 adjacent to the main bore 22. The spring bore 42 includes a spring mount 48 at one end. Two access slots 44 and 46 are diametrically placed to either side of the spring bore 42. The access slot 46 shares the wall of the main bore as well.

The syringe carriage 28 includes a spring stop 50 which extends across the spring bore 42. The end of the slots 44 and 46 form a carriage stop by interfering with the movement of the spring stop 50 riding within the access slots 44 and 46. The access slot 44 includes a latch shoulder 52 extending laterally from the slot 44. The end of the spring stop 50 extends outwardly of the spring bore 42 to define a latch with the latch shoulder 52 operatively between the housing 20 and the carriage 28. Manipulation of this distal end of the spring stop 50 relative to the latch shoulder 52 will result in the spring stop 50 moving from the latch shoulder 52 into the longitudinal portion of the access slot 44. The syringe carriage 28 is then free to move longitudinally within the main barrel 22 of the housing 20. Clearance is also provided in the access slot 46 for this motion of the spring stop 50 extending therethrough.

To avoid inadvertent actuation of the system, a lock 54 is slidably arranged on the spring bore 42. The lock 54 is preferably U-shaped and rides in slots provided on the spring bore 42 at about the intersection of the spring bore 42 with the main bore 22. The lock 54 is able to slide into an interfering relationship with the extension of the spring stop 50 outwardly of the spring bore 42. This interference prevents actuation of the system. The lock 54 can then be purposefully slide from the interfering relationship for actuation.

An insertion spring 56 is positioned within the spring bore 42. The spring bore 42 includes the spring mount 58 at one end to accommodate the spring 56. The spring 56 is preferably a compression coil spring which is maintained in compression between the spring mount 48 and the spring stop 50 to bias the syringe carriage 28 to the extended position.

The end of the housing 20 proximal to the needle access opening 40 of the syringe carriage 28 defines a port 60 which is illustrated to receive the access cap end of a standard syringe vial 62. The port 60 is arranged relative to the syringe carriage 28 such that the needle access opening 40 is presented at the port 60 so that the needle 18 of a syringe mounted within the syringe socket 30 will extend through the access cap of the vial 62 for charging of the syringe. The port 60 may also cooperate with the vial 62 to maintain stability of the components during the charging operation.

An additional feature illustrated in the embodiments of FIGS. 1 through 4 is a movably mounted needle guard 64. The needle guard 64 is generally cylindrical and open at both ends to slide over the barrel 10 of a syringe located within the syringe socket 30. A safety spring 66 is contemplated to be integrally formed with the needle guard 64 and to be arranged to zigzag back and forth on one side of the syringe socket 30 to maintain a clear opening through the side opening into the syringe socket 30. This safety spring 66 biases the needle guard 64 to extend from the syringe carriage 28 to cover the needle 18 of a syringe positioned within the syringe socket 30.

In operation, the syringe carriage 28 is preferably placed in the cocked position with the spring stop 50 engaged with the latch shoulder 52. This places the insertion spring 56 in substantial compression for later actuation. The lock 54 is slid into interference with movement of the spring stop 50. A syringe is then loaded laterally into the syringe socket 30 through the side opening defined by the longitudinal housing slot 24 and the longitudinal carriage slot 38. The finger grip flange 12 of the barrel 10 is positioned between the shoulders defined by the inwardly extending flanges 34 and 36.

The needle cover 26 is then removed and a syringe vial 62 is located in the port 60. With this location, the needle 18 penetrates the cap of the vial 62 for charging of the syringe. The needle guard 64 is automatically slid from over the needle 18 by placement of the vial.

Once charged, the inserter is placed at the injection site. The lock 54 is retracted from interference with the spring stop 50. The spring stop 50 is then moved from the latch shoulder 52 and the insertion automatically and rapidly follows. The plunger 14 is accessible at the plunger end of the assembly for manual injection. It is also presented for mechanized injection if an automatic injection system is employed on the plunger end of the inserter.

Once the injection is complete, the inserter and syringe are removed and the needle guard 64 again covers the needle. The needle cover 26 may then be replaced on the syringe for safety and the syringe withdrawn laterally from the side opening.

Turning next to the embodiment of FIGS. 5 through 11, an inserter is illustrated with the syringe being loaded axially from the plunger end. A housing 70 is again illustrated to be substantially cylindrical and has a main bore 72. At the end of the main bore 72 proximal the plunger end of the device, an inwardly extending flange 74 defines a spring mount which, together with a spring 78, operates as a carriage stop. At the end of the housing 70 proximal the needle end of the device, an end section 76 is shown to have an increased inside diameter over that of the main portion of the housing 70 to receive a latch assembly.

Figure 6:
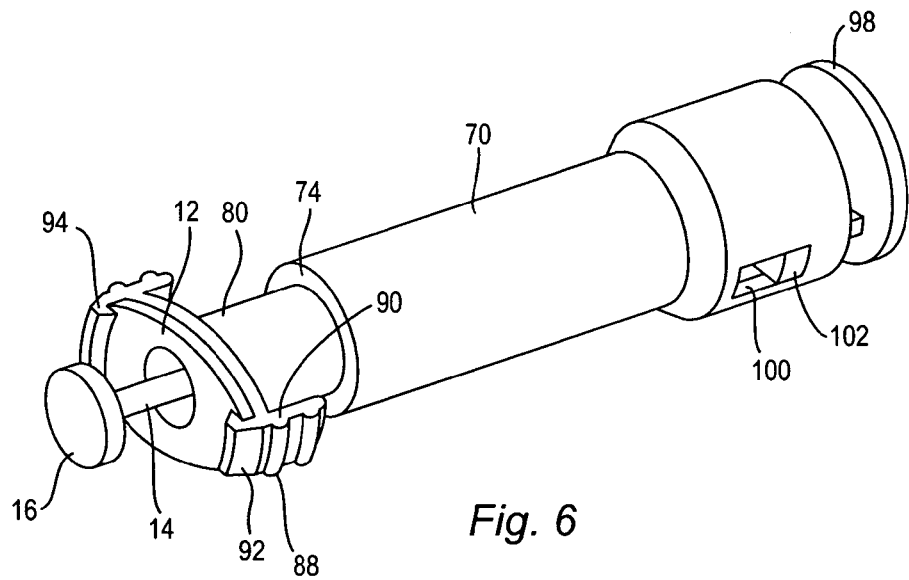
FIG. 6 is a perspective view of the other side of the second syringe insertion system of FIG. 5.
Figure 7:
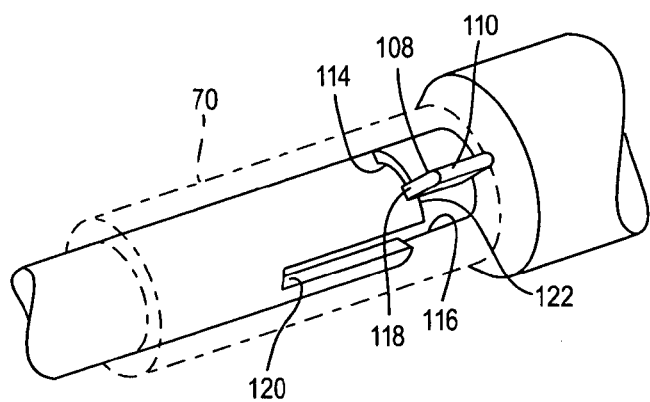
FIG. 7 is a cross-sectional side view of the syringe insertion system of FIG. 5 with the syringe carriage in the cocked position.

The syringe carriage 80 defines a syringe socket 82. The syringe socket 82 includes a plunger access opening 84 which receives the finger grip flange 12. An outwardly extending flange 86 defines a shoulder to receive one side of the finger grip flange 12. Two pivotal clips 88 each effectively employ a living hinge 90. The living hinge 90 mounts a lever 92 having a barrel retention flange 94 which extends into the plunger access opening. On the outer periphery of the syringe carriage 80, a spring stop 96 provides a shoulder to receive a compression spring 78 extending between the spring mount 74 and the spring stop 96. The syringe carriage 80 can assume a cocked position as illustrated in FIG. 6 or an extended position, as illustrated in FIG. 7.

A latch 98 is slidably mounted within the end section 76 of the housing 70. Mounting slots 100 receive fingers 102 which limit movement of the latch 98 between a latched position as illustrated in FIG. 6 and an unlatched position illustrated in FIG. 7. The needle end of the syringe carriage 80 defines a latch shoulder 104. Two catches 106 are shown to be resiliently mounted to the latch 98 for engaging and disengaging the latch shoulder 104 of the syringe carriage 80. A beveled end on each of the catches 106 facilitates more uniform disengagement. The resiliently mounted catches 106 are illustrated in an engaging position in FIGS. 7 and 10 and a disengaging position in FIGS. 8 and 11.

A lock 108 is positioned to pivot about the main axis of the device. The lock includes a tab 110 which extends through an access port 112. The lock 108 has an arcuate body 114 that resides within a cavity 116 about the outer periphery of the syringe carriage 80. An engagement pin 118 extends downwardly from the arcuate body 114. The syringe carriage 80 has a longitudinal slot 120 to receive the engagement pin 118 in a manner that allows longitudinal movement of the syringe carriage 80 in the housing 70. A circumferential notch 122 extending from the longitudinal slot 120 provides a locking shoulder to retain the engagement pin 118 until it is aligned with the longitudinal slot 120 in the unlocked position.

In operation, the levers 92 are pinched toward one another to retract the barrel retention flanges 94. A syringe is then positioned within the syringe socket 82 of the syringe carriage 80. The levers 92 are released to engage the finger grip flange 12 of the barrel 10. The syringe may have been prefilled or may be filled at this time through removal of the needle cover 26 and manipulation of the plunger 14 in association with a standard syringe vial 62.

The syringe carriage 80 is then drawn outwardly from the housing 70 through the plunger end thereof. Once the spring 97 is sufficiently compressed, the engagement pin 118 of the lock 108 is engaged with the circumferential notch 122. The lock 108 may be biased into this position by a spring or other mechanism or may be manually set into the locked position. The latch 98 is then pulled into the latched position. The assembly is placed on the site appropriate for injection and the lock 108 released. The entire device is then forced toward the needle end such that the catches 106 of the latch 98 disengage from the latch shoulder 104. This releases the syringe carriage 80 to move from the cocked position. The spring 97 moves the syringe carriage 80 to the extended position, inserting the needle 18 for the injection. Once completed, the device is withdrawn and the needle cover 26 is replaced.

Figure 8:
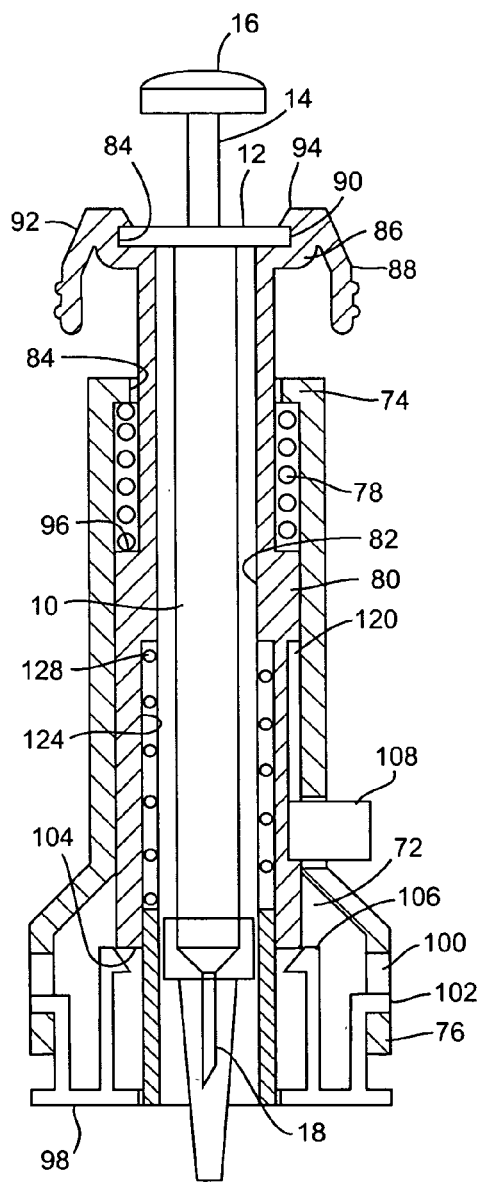
FIG. 8 is a cross-sectional side view as taken in FIG. 7 with the syringe carriage in the extended position.
Figure 9:
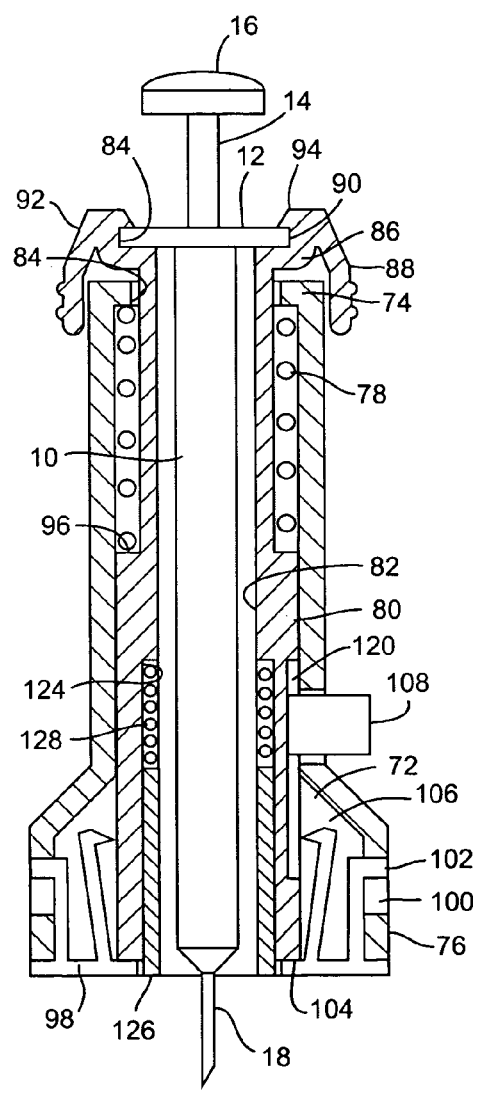
FIG. 9 is a detail in perspective of the system of FIG. 5 with the housing shown in phantom to see the locking mechanism.
Figure 10:
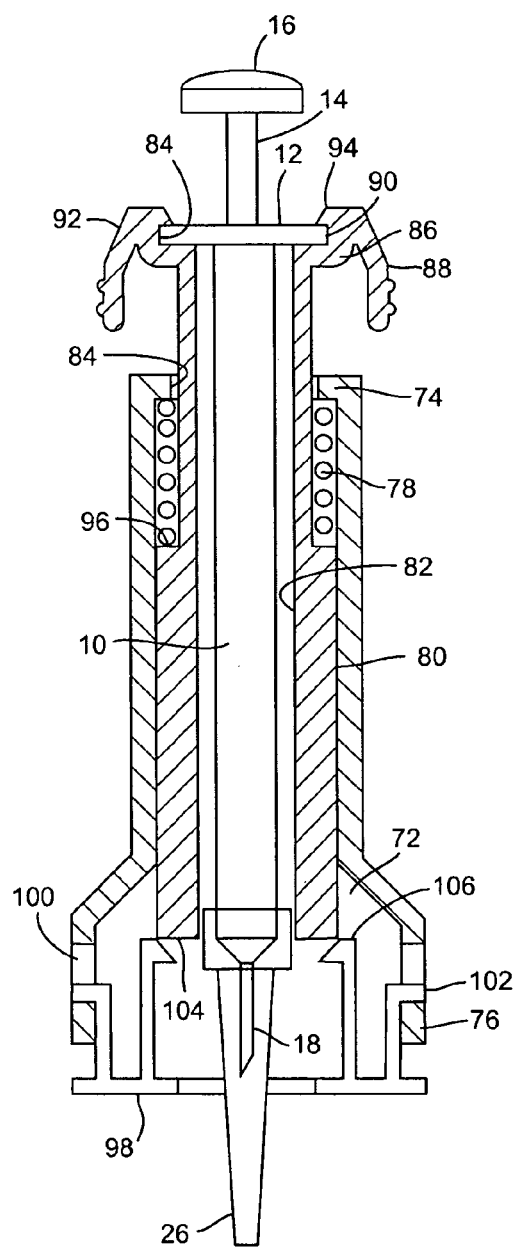
FIG. 10 is a cross-sectional side view of the device of FIG. 5 without a hollow needle guard with the syringe carriage in the cocked position.
Figure 11:
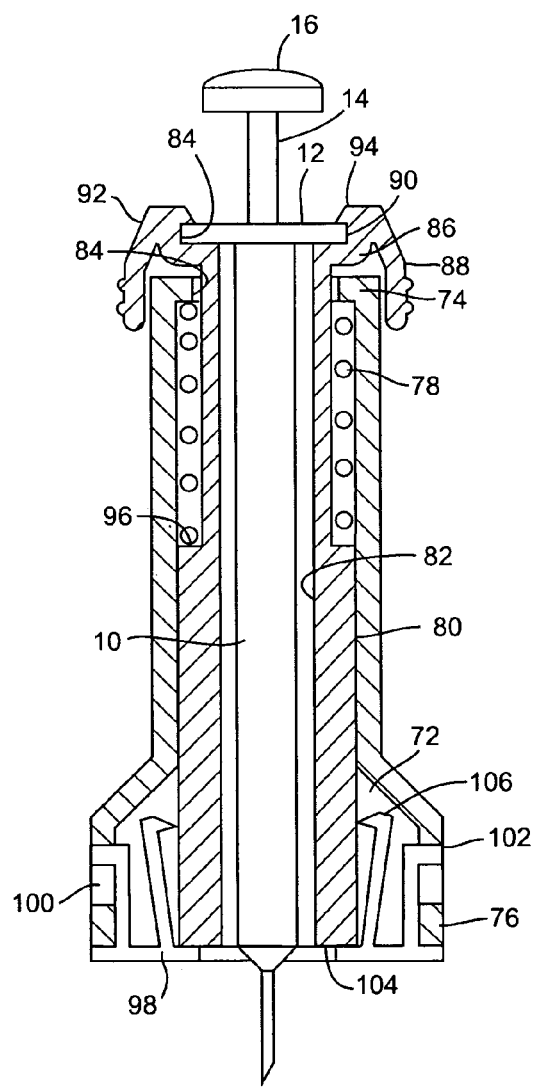
FIG. 11 is a cross-sectional side view of the device of FIG. 5 without a hollow needle guard with the syringe carriage in the extended position.

FIGS. 7 and 8 illustrate another feature which includes an inner annular cavity 124 in the syringe carriage 80 to receive a needle guard 126. The needle guard is like that of the first embodiment but employs a conventional spring 128 to bias the needle guard 126 outwardly to surround the needle.

In each of the embodiments illustrated, the plunger access opening 32 is shown to provide access for forceful extension of the plunger 14. This is advantageous when employing safety syringes which include a needle release mechanism actuated with the plunger forced to the end of the barrel and a needle retraction mechanism operatively engageable with the needle. As the plunger 14 is forced fully into the barrel 10, the needle is released and drawn back into the syringe. By having the plunger end of the syringe carriage 28, 80 outwardly of the housing 20, 70 with the syringe carriage in either the cocked or extended positions, the access to fully manipulate a safety syringe is provided. Safety syringes having a capability of needle retraction upon full advance of the plunger are illustrated in the aforementioned U.S. Pat. No. 5,389,076 and U.S. Pat. No. 6,050,977.

Thus, insertion devices for the placement of a standard syringe for an injection are disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. An inserter for a syringe having a barrel, a plunger slidable in and extending from one end of the barrel and a needle at the other end of the barrel, comprising
   a housing including a main bore and at least a first terminal end;
   a syringe carriage movably mounted within the main bore between a cocked position distal the first terminal end and an extended position proximal the first terminal end and including a syringe socket for selectively retaining the barrel;
   an insertion spring biasing the carriage toward the extended position;
   a latch selectively retaining the carriage in the cocked position;
   a movably mounted needle guard at the first terminal end, the movably mounted needle guard being slidably mounted to the syringe carriage and including a safety spring operatively connected between the syringe carriage and the needle guard biasing the needle guard to extend from the syringe carriage proximal the first terminal end.

2. The inserter of claim 1
   the housing defining a port at the first terminal end sized to receive an access cap of a standard syringe vial.

3. The inserter of claim 2, the port presenting the access cap to receive the needle of a syringe in the syringe socket with the syringe carriage in the cocked position.

4. The inserter of claim 2 further comprising
   a movably mounted needle guard at the first terminal end.

5. The inserter of claim 4, the movably mounted needle guard being slidably mounted to the syringe carriage and including a safety spring operatively between the syringe carriage and the needle guard biasing the needle guard to extend from the syringe carriage proximal the first terminal end.

6. An inserter for a syringe having a barrel, a plunger slidable in and extending from one end of the barrel and a needle at the other end of the barrel, comprising
   a housing including a main bore and at least a first terminal end;
   a syringe carriage movably mounted within the main bore between a cocked position distal the first terminal end and an extended position proximal the first terminal end and including a syringe socket for selectively retaining the barrel;
   an insertion spring biasing the carriage toward the extended position;
   a latch selectively retaining the carriage in the cocked position, the latch being movably mounted relative to the housing at the first terminal end of the housing between a latched position extending from the housing and an unlatched position retracted toward the housing.

7. The inserter of claim 6, the syringe carriage further including a plunger access opening to the syringe socket proximal a second terminal end of the at least first terminal end of the housing and two pivotal clips each having a flange extendable into the plunger access opening to retain the barrel and a lever to actuate the flange.

8. The inserter of claim 6 further comprising
   a movably mounted needle guard at the first terminal end.

9. The inserter of claim 8, the movably mounted needle guard being slidably mounted to the syringe carriage and including a safety spring operatively between the syringe carriage and the needle guard biasing the needle guard to extend from the syringe carriage proximal the first terminal end.

10. An inserter for a syringe having a barrel, a finger grip flange on the barrel, a plunger slidable in and extending from one end of the barrel, a needle at the other end of the barrel, a needle retraction mechanism operatively engageable with the needle, comprising
    a housing including a main bore, a first terminal end and a second terminal end;
    a syringe carriage movably mounted within the main bore between a cocked position distal the first terminal end and an extended position proximal the first terminal end and including a syringe socket for selectively retaining the barrel and a plunger access opening to the syringe socket proximal the second terminal end providing access for forceful extension of the plunger to the end of the barrel, the plunger access opening being outwardly of the main bore in both the cocked position and the extended position;
    an insertion spring biasing the carriage toward the extended position;
    a latch selectively retaining the carriage in the cocked position, the latch being operatively between the housing and the syringe carriage and movably mounted relative to the housing at the end of the main bore proximal the first terminal end between a latched position extending from the housing and an unlatched position retracted toward the housing.

11. The inserter of claim 10, the syringe carriage further including a first flange extending into the socket at the plunger access opening.

12. The inserter of claim 11, the syringe carriage further including a second flange extending into the socket, the first and second flanges being spaced to closely capture the finger grip flange.

13. The inserter of claim 10, the housing defining a port at the first terminal end sized to receive an access cap of a standard syringe vial.

14. The inserter of claim 13, the port presenting the access cap to receive the needle of a syringe in the syringe socket with the syringe carriage in the cocked position.

15. The inserter of claim 10, the syringe carriage further including two pivotal clips each having a barrel retention flange extendable into the plunger access opening to retain the finger grip flange and a lever to actuate the flange.

16. The inserter of claim 15, the clips further having a living hinge integral with the syringe carriage.

* * * * *